US011701261B2

(12) United States Patent
Mondal et al.

(10) Patent No.: US 11,701,261 B2
(45) Date of Patent: *Jul. 18, 2023

(54) MEDICAL DEVICE CONTAINING A MULTI-PLY KNIT FABRIC (71) Applicant: Milliken & Company, Spartanburg, SC (US)

(72) Inventors: Rajib Mondal, Greer, SC (US); Thomas C. Wiles, Easley, SC (US); Petr Valenta, Greer, SC (US); James A Rogers, Greenville, SC (US); Emily W. Michaels, Taylors, SC (US); Robert D. Miller, Piedmont, SC (US)

(73) Assignee: Milliken & Company, Spartanburg, SC (US)

( * ) Notice: Subject to any disclaimer, the term of this patent is extended or adjusted under 35 U.S.C. 154(b) by 800 days.

This patent is subject to a terminal disclaimer.

(21) Appl. No.: 16/580,417

(22) Filed: Sep. 24, 2019

(65) Prior Publication Data

US 2020/0107962 A1 Apr. 9, 2020

Related U.S. Application Data (60) Provisional application No. 62/741,305, filed on Oct. 4, 2018.

(51) Int. Cl.
*A61F 13/00* (2006.01)
*A61F 13/04* (2006.01)
(Continued)

(52) U.S. Cl.
CPC .. *A61F 13/00017* (2013.01); *A61F 13/00029* (2013.01); *A61F 13/00063* (2013.01);
(Continued)

(58) Field of Classification Search
CPC .......... A61F 13/00017; A61F 13/00029; A61F 13/00063; A61F 13/04; A61H 9/0057;
(Continued)

(56) References Cited

U.S. PATENT DOCUMENTS 2,804,886 A 9/1957 White ........................ 139/420
2,862,283 A 12/1958 Rasero .......................... 28/80
(Continued)

FOREIGN PATENT DOCUMENTS

CN 103572454 2/2014
EP 202897 11/1986
(Continued)

OTHER PUBLICATIONS

Patent Cooperation Treaty PCT International Search Report, dated Jan. 8, 2020. International Application No. PCT/US2019/054341. International Filing Date: Oct. 2, 2019.

*Primary Examiner* — Yashita Sharma
(74) *Attorney, Agent, or Firm* — Cheryl J. Brickey (57) ABSTRACT A medical device comprising a device that covers at least a portion of a patient's skin and has an inner surface designed to be in contact with the patient's skin. It contains a multi-ply knit fabric that contains a first knit ply and a second knit ply. The first knit ply contains a plurality of first yarns and forms the upper surface of the fabric. The second knit ply contains a plurality of polytetrafluoroethylene (PTFE) yarns which forms the lower surface of the fabric. The first and second ply are integrated through combined portions formed by interlacing first yarns among the PTFE yarns, interlacing PTFE yarns among the first yarns, and interlacing a plurality of third yarns among the first and the PTFE yarns. The multi-ply knit fabric also contains a
(Continued)

composition comprising at least one silver ion-containing compound on at least the upper surface of the multi-ply knit fabric.

19 Claims, 7 Drawing Sheets

(51) Int. Cl.
    *A61H 9/00* (2006.01)
    *D04B 1/16* (2006.01)
    *D04B 1/22* (2006.01)
    *D04B 21/16* (2006.01)
    *D04B 21/20* (2006.01)

(52) U.S. Cl.
    CPC .......... *A61F 13/04* (2013.01); *A61H 9/0057* (2013.01); *D04B 1/16* (2013.01); *D04B 1/22* (2013.01); *D04B 21/16* (2013.01); *D04B 21/20* (2013.01); *D10B 2321/042* (2013.01); *D10B 2509/022* (2013.01)

(58) Field of Classification Search
    CPC . D04B 1/16; D04B 1/22; D04B 21/16; D04B 21/20; D10B 2321/042; D10B 2509/022; A61L 15/26; A61L 15/46; A61L 27/16; A61L 27/18; A61L 27/54; A61L 27/56; A61L 2300/104; A61L 15/24
    See application file for complete search history.

(56) References Cited

U.S. PATENT DOCUMENTS

| | | | |
|---|---|---|---|
| 4,168,298 A | 9/1979 | Fitzgerald | 139/420 R |
| 4,569,088 A | 2/1986 | Frankenburg et al. | 2/81 |
| 4,999,243 A | 3/1991 | Maeda | 428/372 |
| 5,735,145 A | 4/1998 | Pernick | 66/196 |
| 5,740,551 A | 4/1998 | Walker | 2/16 |
| 6,061,829 A | 5/2000 | Gunn | 2/69 |
| 6,634,190 B2 | 10/2003 | Didier-Laurent | 66/196 |
| 6,708,348 B1 | 3/2004 | Romay | 2/239 |
| 6,918,140 B1 | 7/2005 | Cooper | 2/228 |
| 7,069,600 B1 | 7/2006 | Romay | 2/239 |
| 7,213,420 B2 | 5/2007 | Lynch et al. | 66/186 |
| 8,440,119 B2 | 5/2013 | Ackroyd et al. | 264/78 |
| 8,813,525 B2 | 8/2014 | Ayers et al. | 66/194 |
| 10,472,748 B2 | 11/2019 | Mondal et al. | |
| 2003/0089136 A1 | 5/2003 | Lynch et al. | 66/187 |
| 2006/0085894 A1 | 4/2006 | Yakopson et al. | 2/239 |
| 2007/0093162 A1 | 4/2007 | Holcombe et al. | 442/208 |
| 2008/0121305 A1 | 5/2008 | Metzger | 139/421 |
| 2011/0208101 A1 | 8/2011 | Keller et al. | 602/44 |
| 2012/0310186 A1 | 12/2012 | Moghe et al. | 604/304 |
| 2016/0353810 A1 | 12/2016 | Barnes et al. | |
| 2018/0290425 A1 | 10/2018 | Mondal | |

FOREIGN PATENT DOCUMENTS

| | | |
|---|---|---|
| FR | 2 570 935 | 4/1986 |
| GB | 2 074 029 | 10/1981 |
| WO | WO 2003/031700 | 4/2003 |
| WO | WO 2003/040447 | 5/2003 |
| WO | WO 2011/114107 | 9/2011 |

| FEEDS | BACK SIDE | | | | FRONT SIDE | | | |
|---|---|---|---|---|---|---|---|---|
| 1 | X | X | X | X | | | ● | |
| 2 | | | | | X | X | X | X |
| 3 | X | X | X | X | | | ● | |
| 4 | | | | | X | X | X | X |
| 5 | X | X | X | X | ● | | | |
| 6 | | | | | X | X | X | X |
| 7 | X | X | X | X | ● | | | |
| 8 | | | | | X | X | X | X |

*FIG. -6-*

MEDICAL DEVICE CONTAINING A MULTI-PLY KNIT FABRIC

RELATED APPLICATIONS

This application claims priority to U.S. Provisional Patent Application 62/741,305, filed on Oct. 4, 2018, which is herein incorporated by reference in its entirety.

TECHNICAL FIELD OF THE INVENTION

The present invention is directed towards wound dressing systems, more particularly to wound dressing systems containing multi-ply knit fabrics where one of the plies contains polytetrafluoroethylene (PTFE) yarns.

BACKGROUND

In the medical field, and in the area of wound care particularly, it is well-established that many factors, including the amount of moisture present at a wound site, affects how quickly a wound will heal. Generally speaking, having an excessive amount of moisture present at a wound site, especially when combined with the warm environment provided by the body, leads to undesirable bacteria growth and production of protease enzymes in the wound. Such growth can cause further damage to healthy cells and delay the healing process. However, insufficient moisture at the wound site can cause eschar (scab) formation and scarring and may cause the wound care device, or medical dressing, to adhere to the wound. If the dressing adheres to the wound, subsequent removal of the dressing may cause undue discomfort to the patient as well as disrupt newly granulated tissue. Infection of the wound may also be compounded when a medical dressing is removed, and portions of the dressing remain behind in the wound itself, particularly if the dressing is already colonized with pathogenic microbes. Thus, it is important that the dressing maintains its physical integrity when exposed to stress, such as during removal from the wound, in order to prevent additional complications and delays in healing.

It is desirable to have a dressing system that renasfer excess moisture as well as does not stick to the wound, is low friction, is hypoallergenic, inert, and optionally create a dressing that is cool to the patient's touch.

BRIEF SUMMARY OF THE INVENTION

A medical device comprising a device that covers at least a portion of a patient's skin. The device has an inner surface and an outer surface, where the inner surface is designed to be in contact with the patient's skin. The inner surface of the device comprises a multi-ply knit fabric having an upper and lower surface and a length and width. The multi-ply knit fabric has an upper and lower surface and contains a first knit ply and a second knit ply. The first knit ply contains a plurality of first yarns and forms the upper surface of the fabric. The second knit ply contains a plurality of polytetrafluoroethylene (PTFE) yarns, where the PTFE yarns have a density of about 2 to 2.3 g/cm$^3$, a transmission in the IR region of 8-10 µm at least about 40%, and a thermal conductivity of at least about 0.2 W/(m·K). The second knit ply forms the lower surface of the fabric. The first ply and the second ply are integrated through combined portions formed by at least one method selected from the group consisting of interlacing first yarns among the PTFE yarns of the second knit ply, interlacing PTFE yarns among the first yarns of the first knit ply, and interlacing a plurality of third yarns among the first yarns of the first knit ply and the PTFE yarns of the second knit ply. The multi-ply knit fabric also contains a composition comprising at least one silver ion-containing compound on at least the upper surface of the multi-ply knit fabric.

DETAILED DESCRIPTION

Figure 1A:
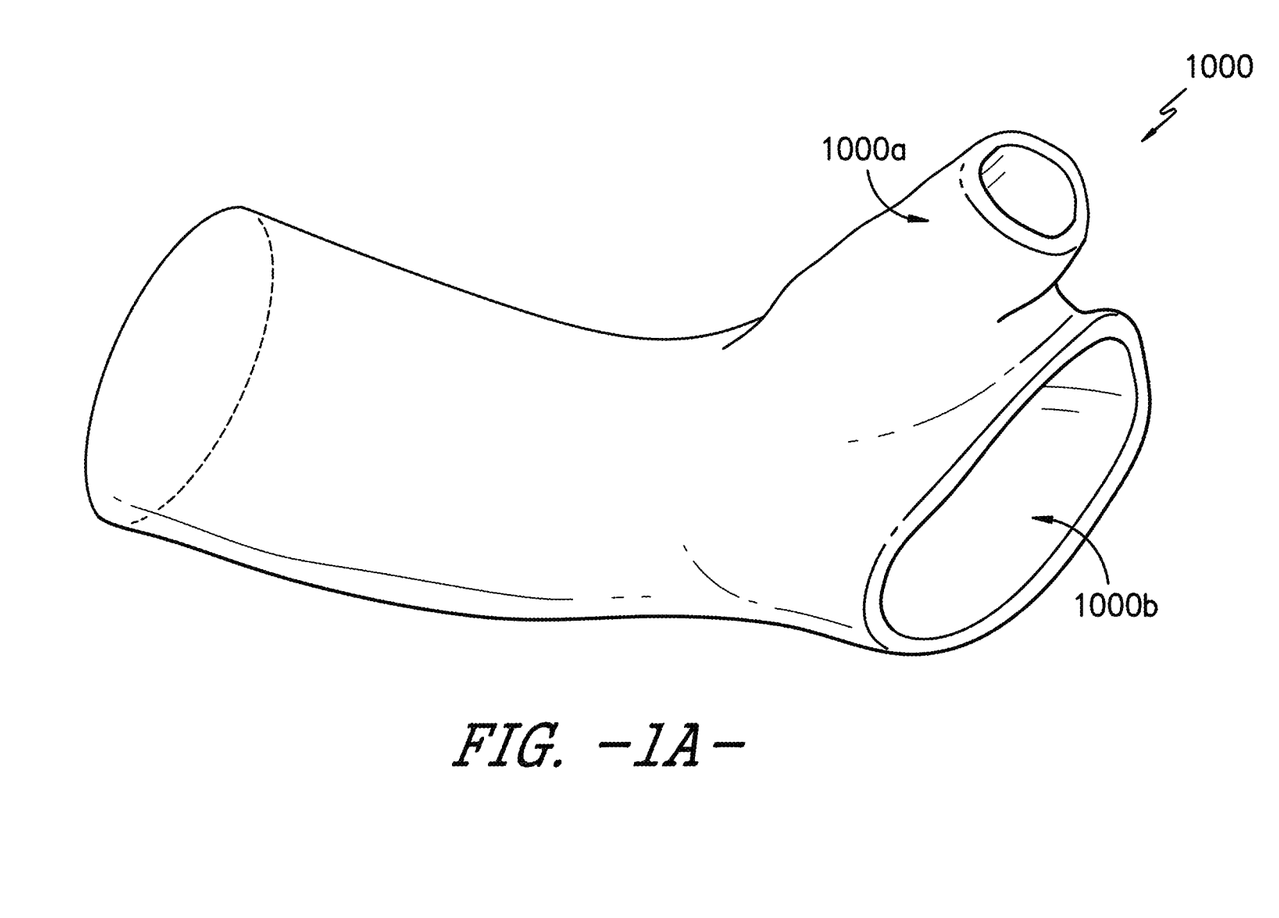
FIG. 1A is an illustration of one embodiment of a medical device containing a multi-ply knit fabric.

Referring now to FIG. 1A, there is shown an illustration of one embodiment of the medical device 1000. In FIG. 1A, the medical device is a wrist case, but it can be any suitable medical device that is located on or adjacent a patient's skin. The medical device has an inner surface 1000b and an outer surface 1000a. Then inner surface 1000b is designed to be in contact with the patient's skin.

In one embodiment, the medical device is an immobilizing device that is used to immobilize a portion of the patient's body. A cast and splint are examples of this type of device. In another embodiment, the medical device is compression device which is used to compress portions of the patient's body. An elastic bandage would be an example of a compression device. In another embodiment, the medical device is a decompression device which may use suction or a vacuum to decompress a portion of the patient's body.

The medical device 1000 has a multi-ply knit fabric layer 10 forming the inner surface 1000b of the device 1000. The multi-ply knit fabric 10 can be been in FIG. 1B.

Figure 1B:
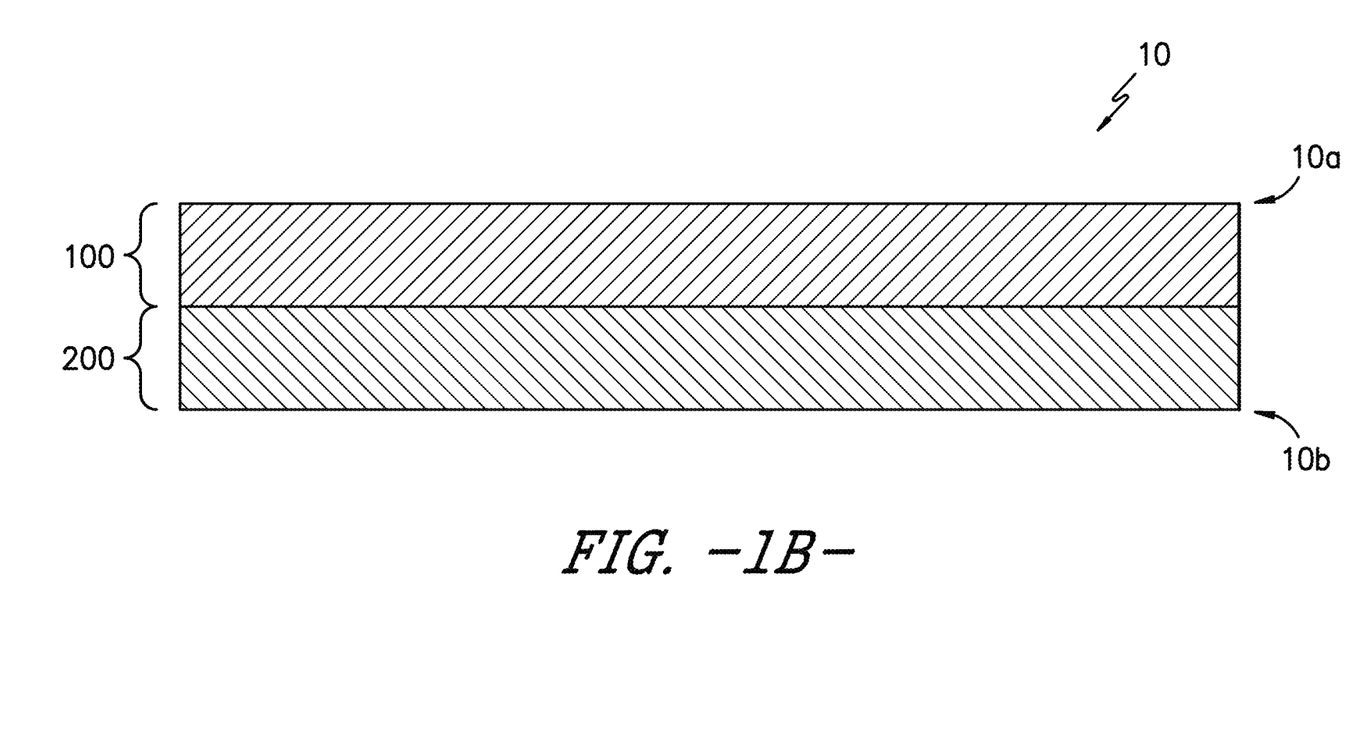
FIG. 1B is a cross-sectional illustration of one embodiment of a multi-ply knit fabric.
Figure 2:
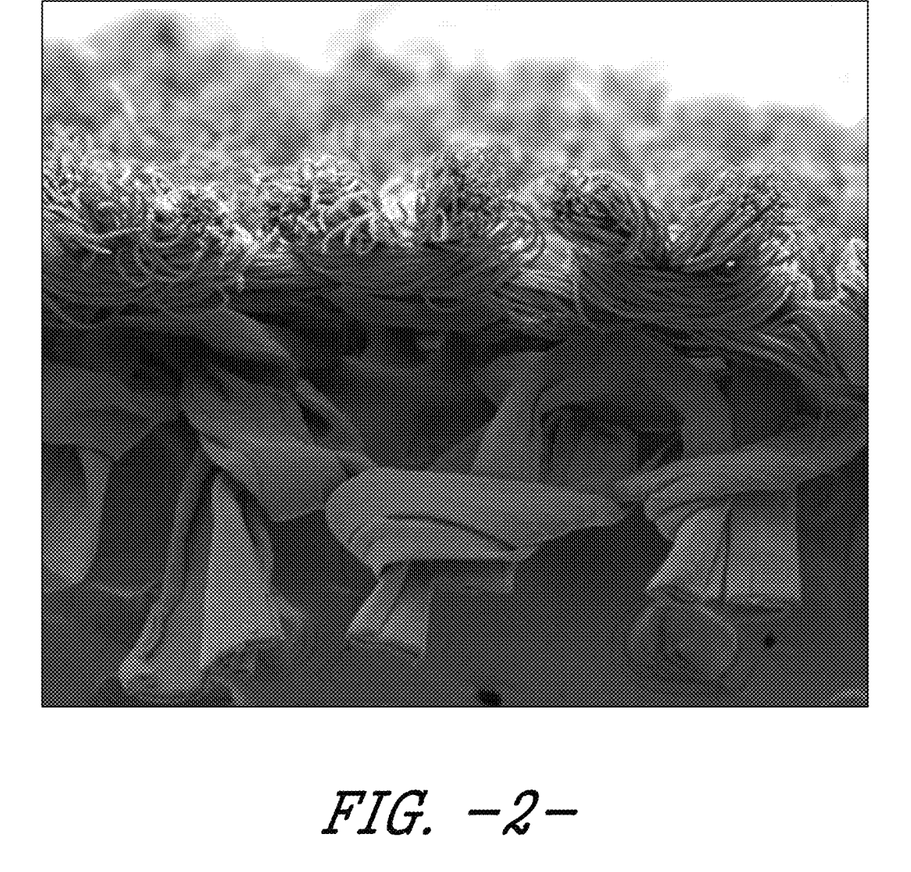
FIG. 2 is a is a photo-micrograph of a cross-section of the multi-ply knit fabric according to one embodiment of the invention.
Figure 3:
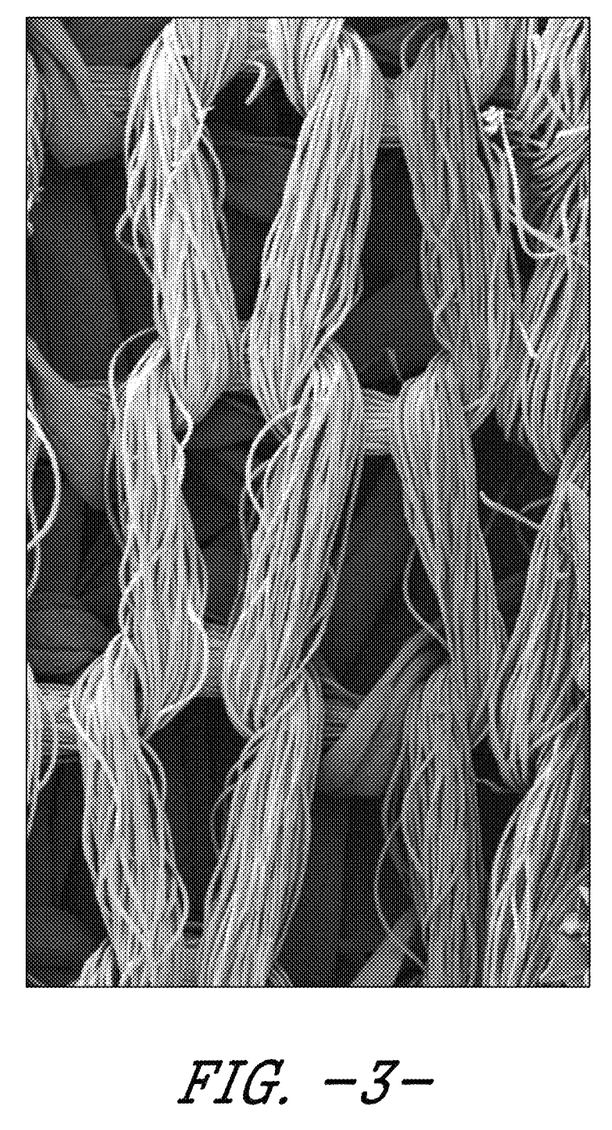
FIG. 3 is a photomicrograph of the upper surface of the multi-ply knit fabric of FIG. 2.
Figure 4:
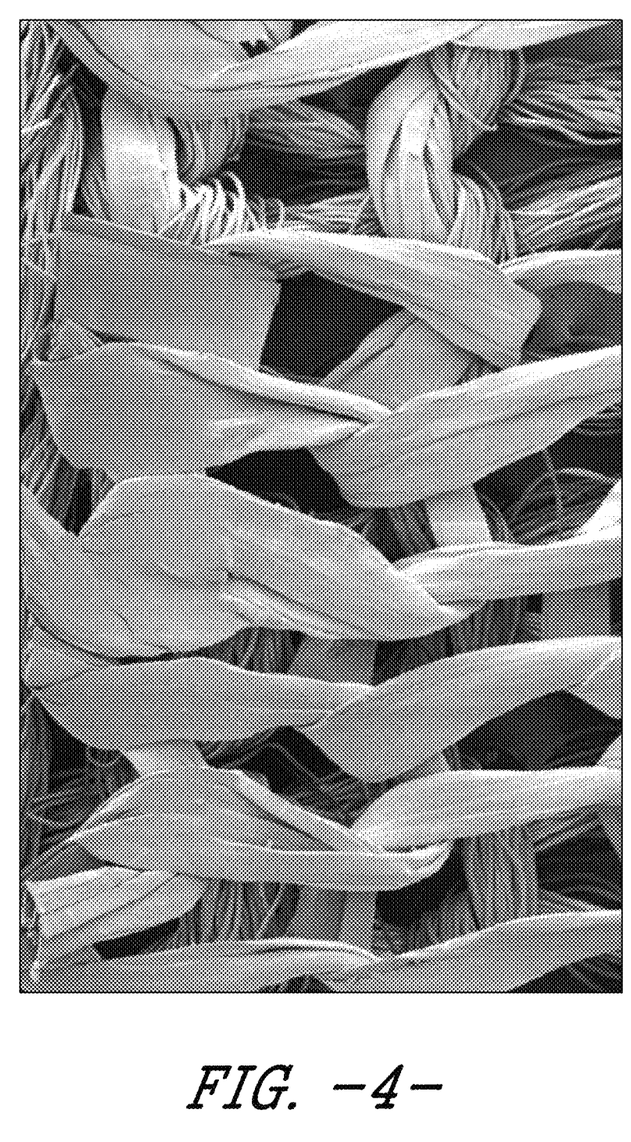
FIG. 4 is a photomicrograph of the lower surface of the multi-ply knit fabric of FIG. 2.

The knit fabric 10 has an upper surface 10a and a lower surface 10b. When the fabric 10 is placed into the system, preferably the lower surface 10b would be facing the patient and upper surface 10a would be facing away from the patient. The knit fabric 10 of FIG. 1B is shown containing 2 plies; a first knit ply 100 and a second knit ply 200. The knit fabric 10 is a unitary material that is formed together in a knitting machine with the two plies separated by a dashed line. The plies 100 and 200 are not formed as discrete knit layers and then joined together in a later operation. FIG. 2 is a photomicrograph of a cross-section of one embodiment of the multi-ply knit fabric 10. FIG. 3 is a photomicrograph of the upper surface (first knit ply) of the multi-ply knit fabric of FIG. 2 and FIG. 4 is a photomicrograph of the lower surface (second knit ply) of the multi-ply knit fabric of FIG. 2.

The multi-ply knit fabric 10 may be made by any suitable knitting method, including both warp knitting and weft (or circular) knitting. Circular knitting is preferred in some embodiments, as it tends to be more cost efficient. The two plies may have the same knit construction or different.

The first knit ply 100 comprising a plurality of first yarns and forms the upper surface 10a of the fabric 10. The first yarns in the first knit ply 100 may be any suitable yarn. "Yarn", in this application, as used herein includes a monofilament elongated body, a multifilament elongated body, ribbon, strip, yarn, tape, fiber and the like. The first knit ply 100 may contain one type of yarn or a plurality of any one or combination of the above. The yarns may be of any suitable form such as spun staple yarn, monofilament, or multifilament, single component, bi-component, or multi-component, and have any suitable cross-section shape such as circular, multi-lobal, square or rectangular (tape), and oval. In one preferred embodiment, the first ply 100 contains multifilament polyester yarns as these have been shown to have good performance at low cost.

The first knit ply may have any suitable knit pattern and be formed by any suitable yarns. The yarns in the first ply may be a single plurality or type of yarn (e.g., the fabric can be formed solely from yarns comprising a blend of cellulosic yarns and synthetic yarns, such as polyamide yarns), or the textile can be formed from several pluralities or different types of yarns (e.g., the fabric can be formed from a first plurality of yarns comprising cellulosic yarns and polyamide yarns and a second plurality of yarns comprising an inherent flame resistant yarn). The yarns may be formed of (but are not limited to) cellulosic yarns (such as cotton, rayon, linen, jute, hemp, cellulose acetate, and combinations, mixtures, or blends thereof), polyester yarns (e.g., poly(ethylene terephthalate) yarns, poly(propylene terephthalate) (PET) yarns, poly(trimethylene terephthalate) yarns), poly(butylene terephthalate) yarns, and blends thereof), polyamide yarns (e.g., nylon 6 yarns, nylon 6,6 yarns, nylon 4,6 yarns, and nylon 12 yarns), polyvinyl alcohol yarns, an elastic polyester-polyurethane copolymer (SPANDEX®), flame-resistant meta-aramid (NOMEX®) and combinations, mixtures, or blends thereof.

The second knit ply 200 comprising a plurality of polytetrafluoroethylene (PTFE) yarns and forms the lower surface 10b of the fabric 10. Preferably, if the fabric 10 is made into a garment, the second knit ply 200 faces the wearer and is preferably in direct contact with the wearer's skin. The lower surface 10b of the fabric 10 has a surface roughness of less than about 500 μm, preferably less than about 200 μm. PTFE yarn could be of any denier or sizes. In one preferred embodiment, 220 denier PTFE is used and in another embodiment, 100 denier PTFE yarn is used. However, depending on the desired weight (oz per sq. yd) and other properties, the denier of the PTFE yarn could be smaller or larger.

The PTFE yarns have a density of about 2 to 2.5 $g/cm^3$, more preferably about 2.0 to 2.3 $g/cm^3$, more preferably about 2.15 to 2.25 $g/cm^3$. Typical textile yarns, such polyester, nylon or cotton have density less than 1.6 $g/cm^3$. The PTFE yarns have a transmission in the IR region of 8-10 μm at least about 40%, more preferably at least about 60%. In case of polyester, it has C—O stretching frequency from 7.7-10 micron and C—H bending from 7.8-14.5 micron, which leads to reduced transmission, 20% or less in the IR region of 8-10 micron. It has been shown that this 20% of less transmission in the IR region of 8-10 microns produces a fabric with less active cooling. The PTFE yarns also have a thermal conductivity of at least about 0.2 W/(m·K), more preferably at least about 0.23 W/(m·K), more preferably at least about 0.25 W/(m·K). Polyester yarn has much lower thermal conductivity of ~0.15 W/(m·K). Preferably, the PTFE yarns have a generally rectangular cross-sectional shape.

Figure 5:
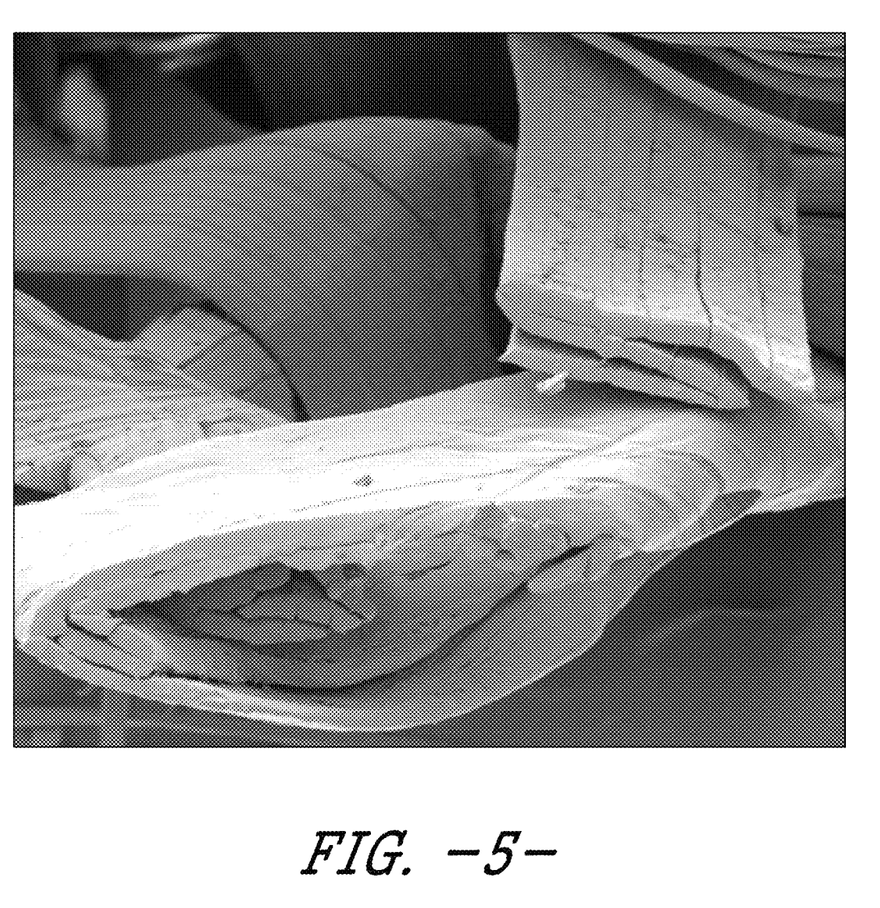
FIG. 5 is a photomicrograph of some PTFE yarns in the knit fabric.

When measuring aspect ratio, the cross-section of the yarn is measured across the entire width (even if the tape is folded onto itself). In one embodiment, the PTFE yarns have a cross-section aspect ratio across the entire width of between about 20:1 to 100:1. Typical flat polyester has the aspect ratio of less than 5:1. Typical PTFE yarn is used in a folded state, meaning that there are fold lines running along the length of the tape yarns and portions of the yarn lay on other portions of the yarn (sometimes like an accordion) such as can be seen in FIG. 5. If the aspect ratio is measured of the folded PTFE yarn, the aspect ratio would be between about 10:1 to 2:1.

The first 100 and second 200 plies are integrated through combined portions, this is preferably done at the time of knitting such that the fabric 10 is created as a multi-ply knit fabric, not as two separate knit fabrics that are then joined in a subsequent process step. This integration may be from one of the following methods, or a combination of the methods.

The first method is interlacing first yarns from the first ply among the PTFE yarns of the second knit ply, meaning that a portion of the first yarns from the first ply leave the first ply, travel down into the second ply where they are interlaced with yarns within the second ply, and then travel back up to the first ply.

The second method is interlacing PTFE yarns from the second ply among the first yarns of the first knit ply, meaning that a portion of the PTFE yarns from the second ply leave the second ply, travel up into the first ply where they are interlaced with yarns within the first ply, and then travel back down to the second ply to the first ply.

The third method is interlacing a plurality of third yarns among the first yarns of the first knit ply and the PTFE yarns of the second knit ply. This means that a third yarn (which may be the same or different yarn than the first yarns and/or PTFE) travels between the plies, interlacing with yarns from both plies and in essence, tying them together. Preferably, the third yarns comprise PTFE yarns.

In a preferred embodiment, the second method is used to interlace the first 100 and second 200 ply together. This method is preferred because of the lower complexity during the knitting process using the circular knitting.

In one embodiment, the multi-ply knit fabric is made using what is referred to as a flat back mesh construction. In this construction, the yarns are evenly spaced on the flat side, while the yarns are not spaced evenly on the mesh side (PTFE side) (open). The knitting diagram for this construction can be seen in FIG. 6. Preferably, the second ply is more open than the first ply, meaning that there are gaps in the second ply (so that when looking at the lower surface of the fabric 10, some of the first ply 100 can be seen through the gaps in the second ply 200. The mesh allows the moisture from the human skin to transport more efficiently to the environment, while minimizing the materials use. PTFE is preferably used in the mesh side. In the mesh side, the gaps between two yarns could be up to 0.5-1 mm.

Thickness of the both faces are almost equally distributed, while contents of different yarns are controlled by changing the gap between the yarns in the mesh side. Tightness of the knitting is also controlled to achieve the total fabric thickness. Typical fabric thickness can be varied from 0.25-0.8 mm.

In one embodiment, the fabric 10 contains a third knit layer. Preferably, this third knit layer is on the first ply (on the side opposite to the second ply) or between the first and second plies. When the fabric 10 contains a third ply, the second play preferably still forms the lower surface 10b of the fabric 10. The third layer may be knitted from any of the materials (or combinations of materials) disclosed as suitable materials for the first 100 or second 200 ply and is preferably knit as the same time and integral with the first and second plies.

It is preferred to have the amount of PTFE yarns in the fabric 10 (as a whole) be as low as possible due to the cost of the PTFE yarns in relation to the other yarns in the fabric 10. In one embodiment, the fabric 10 comprises less than about 75% by weight PTFE yarns. In another embodiment, the fabric 10 comprises less than about 50% by weight PTFE yarns. In another embodiment, the fabric 10 comprises between about 5 and 75% by weight PTFE yarns. It is believed to be most important to concentrate the PTFE yarns on the lower surface 10b of the fabric 10 to maximize their cooling effect, the non-stick, and other desired properties. In one embodiment, the second knit ply comprises at least about 90% by weight PTFE yarns. In another embodiment, the lower surface 10b comprises at least about 90% by weight PTFE yarns.

The multi-ply knit fabric also preferably contains a composition comprising at least one silver ion-containing compound on at least the upper surface of the multi-ply knit fabric. In another embodiment, the knit fabric is dip coated to the composition so that all of the surfaces of the yarns within the knit fabric are exposed to the composition. Typically, the composition sticks very minimally to almost not at all to the PTFE yarns.

The silver ion-containing compound is preferably selected from the group consisting of silver ion exchange materials (e.g. silver zirconium phosphates, silver calcium phosphates and silver zeolites), silver particles (e.g. silver metal, nanosilver, colloidal silver), silver salts (e.g. AgCl, $Ag_2CO_3$), silver glass, and mixtures thereof. One preferred silver ion-containing compound is an antimicrobial silver sodium hydrogen zirconium phosphate available from Milliken & Company of Spartanburg, S.C., sold under the tradename AlphaSan®. Other potentially preferred silver-containing antimicrobials suitable for use herein—including silver zeolites, such as a silver ion-loaded zeolite available from Sinanen Co., Ltd. of Tokyo, Japan under the tradename Zeomic®, and silver glass, such as those available from Ishizuka Glass Co., Ltd. of Japan under the tradename Ionpure® may be utilized either in addition to, or as a substitute for, the preferred species listed above. Other silver ion-containing materials may also be used. Various combinations of these silver-containing materials may be made if adjustments to the silver release rate over time are desired.

Generally, the silver-based compound is added in an amount from about 0.01% to about 60% by total weight of the particular finish composition; more preferably, from about 0.05% to about 40%; and most preferably, from about 0.1% to about 30%. The antimicrobial finish itself, including any desired binders, wetting agents, odor absorbing agents, leveling agents, adherents, thickeners, and the like, is added to the substrate in an amount of at least about 0.01% of the total device weight.

A binder material has been found useful in preventing the antimicrobial from flaking off the fabric and onto the wound. Preferably, this component is a polyurethane-based binding agent, although a wide variety of cationic, anionic, and non-ionic binders may also be used, either alone or in combination. Preferably, the binding agent is biocompatible such that is does not cause negative reactions in the wound. In essence, such binders provide durability by adhering the antimicrobial to the target substrate, such as fibers or fabrics, without negatively affecting the release of silver ions to the wound.

Total add-on levels of silver to the target substrate may be 20 ppm or higher. More preferably, total add-on levels of silver may be 200 ppm or higher. Although an upper boundary limit of silver add-on levels to the target substrate has not been determined, consideration of the manufacturing economics and the potential to irritate a sensitive wound site suggests avoiding excessive silver levels.

Silver ion-containing compounds (such as AlphaSan®, Zeomic®, or Ionpure®) may be admixed in an aqueous dispersion with a binder to form a bath into which the knit fabric is immersed. Other similar types of compounds that provide silver ions may also be utilized.

When specific polyurethane-based binder materials are utilized, the antimicrobial characteristics of the treated substrate are effective with regard to the amount of surface available silver that is released to kill bacteria, without altering the color of the treated substrate (that is, while substantially maintaining its original appearance). While it currently appears that the use of polyurethane-based binder resins are preferred due to their allowance of silver release and bio-neutral properties, in practice essentially any effective cationic, anionic, or non-ionic binder resin that is not toxic to the wound may be used.

An acceptable method of providing a durable antimicrobial silver-treated fabric surface is the application of a silver ion-containing compound and polyurethane-based binder resin from a bath mixture. This mixture of antimicrobial compound and binder resin may be applied through any technique as is known in the art, including spraying, dipping, padding, foaming, printing, and the like. By using one or more of these application techniques, a fabric may be treated with the antimicrobial compound and binder resin on only one side of the fabric (e.g. the wound contact surface of a wound care device), or it may be treated on both sides of the fabric.

Preferably, the multi-ply knit fabric (as well as all of the other layers within the systems 500, 900) are sterilized. This sterilization can occur to each layer within the systems before assembly or after the systems are assembled together. Any suitable sterilization method may be used that does not harm or otherwise interfere with the desired properties of the systems. For example, heat, irradiation, or chemicals may be used separately or in combination to sterilize the systems 500, 900.

In one embodiment, the multi-ply knit fabric 10 and/or the systems 500, 900 are non-electrically conductive. "Non-electrically conductive" is defined as having a resistance in ohms per square inch of fabric of greater than about 10,000 ohms, preferably greater than about 100,000 ohms and most preferably greater than about $1 \times 10^9$ ohms, when measured in accordance with AATCC Test Method 76-1978.

Test Methods

Weight of the fabric was measured using ASTM D 3776. Air permeability was measured using ASTM D 737. MVTR was measured ASTM E 96-95: Water Vapor Transmission of Materials, modified procedure B; both Open Jar Method and with the Air Flow method. Q-Max is the measurement of the maximum heat loss that can occur when the skin touching objects or other materials. Larger Q-max, cooler the material, in this case fabric, to human touch. The Kawabata thermal tester (Thermolabo) is used to measure the Q-max. Intrinsic thermal resistance, apparent intrinsic evaporative resistance, and total heat loss are measured using a sweating guarded hot plate using ASTM F1868, Part C.

EXAMPLES

Figure 6:
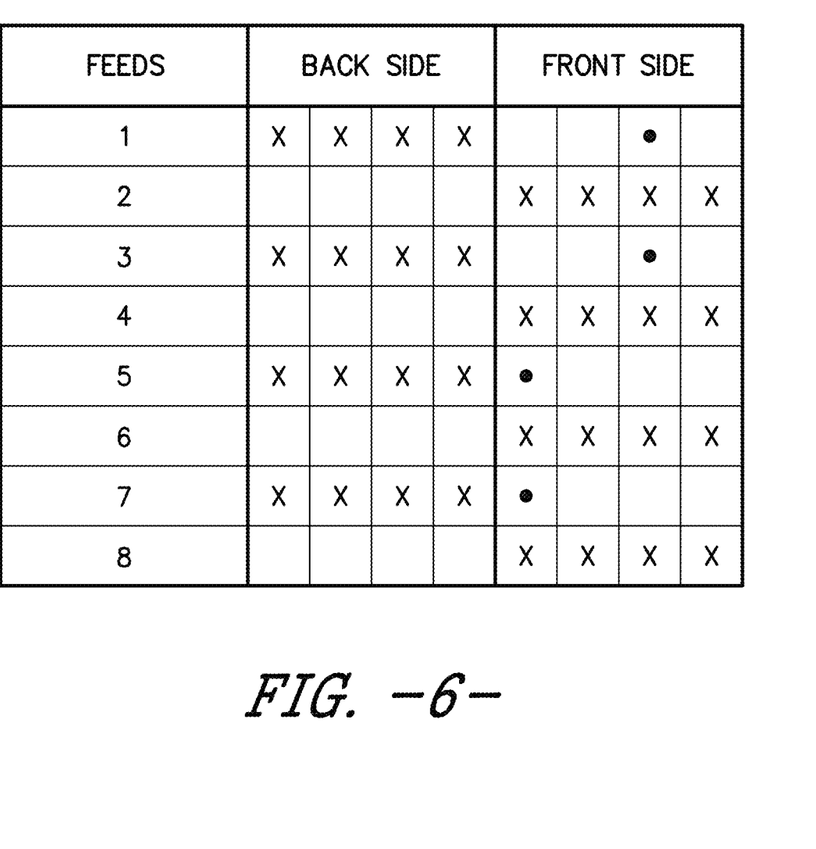
FIG. 6 is a knit diagram of the multi-ply knit fabric according to one embodiment of the invention.

The table below summarizes the 13 examples. The PTFE yarn used was either 220 den (Lenzing™ Profilen FG02 natural) and 100 den (Lenzing™ Profilen FR110 natural). The polyester yarn used was a multi-filament yarns in a 1 ply or 2 ply 70/72 construction. Examples 1-8 were knitted in flat back mesh construction as shown in FIG. 6. Example 9 was a 50/50 PTFE (220 den)/polyester interlock knit and example 10 was a 100% polyester interlock knit. Examples 1-10 were subjected to navy disperse dyeing process and tentering for testing and evaluation. Example 11 was a commercially available fabric from ADIDAS™ called Climachil which is a double knit, bi-ply. The outerply contains typical multifilament round polyester yarn and the inner ply contains multifilament flat polyester yarns.

|  | Yarn content | Polyester yarn type | PTFE yarn type | Ounces per square yard (OSY) oz/yd$^2$ |
|---|---|---|---|---|
| Ex. 1 | 69%/31% PTFE/polyester | 1/70/72 | 220 den | 5.7 |
| Ex. 2 | 53%/47% PTFE/polyester | 2/70/72 | 220 den | 8.8 |
| Ex. 3 | 36%/64% PTFE/polyester | 2/70/72 | 100 den | 6.0 |
| Ex. 4 | 54%/46% PTFE/polyester | 1/70/72 | 100 den | 3.7 |
| Ex. 5 | 77%/23% PTFE/polyester | 1/70/72 | 220 den | 5.5 |
| Ex. 6 | 62%/38% PTFE/polyester | 2/70/72 | 220 den | 7.8 |
| Ex. 7 | 45%/55% PTFE/polyester | 2/70/72 | 100 den | 5.6 |
| Ex. 8 | 63%/37% PTFE/polyester | 1/70/72 | 100 den | 3.3 |
| Ex. 9 | 50%/50% PTFE/polyester | 1/70/72 | 220 den | 6.8 |
| Ex. 10 | 100% Polyester | 1/70/72 and 2/70/72 | — | 4.9 |
| Ex. 11 | See description above | — | — | 4.2 |

The examples were tested for air permeability, moisture vapor transmission rate (MVTR) (ASTM E 96-95: Water Vapor Transmission of Materials, modified procedure B; both Open Jar Method and with the Air Flow) (g/m$^2$/24 hrs) and Q-max (watts/cm$^2$) of back (skin side) and face of the fabrics.

|  | air perm (cfm) | MVTR (Open Jar) g/m$^2$/24 hrs | MVTR (Air Flow) g/m$^2$/24 hrs | Q-max (back) watts/cm$^2$ | Q-max (face) watts/cm$^2$ |
|---|---|---|---|---|---|
| Ex. 1 | 320 | 882.37 | 6090 | 0.213 | 0.114 |
| Ex. 2 | 206 | 879.53 |  | 2.52 | 0.134 |
| Ex. 3 | 235 | 862.51 |  | 0.187 | 0.128 |
| Ex. 4 | 403 | 876.70 |  | 0.167 | 0.113 |
| Ex. 5 | 406 | 848.33 | 6169 | 0.214 | 0.108 |
| Ex. 6 | 227 | 845.49 |  | 0.215 | 0.117 |
| Ex. 7 | 270 | 913.58 | 5888 | 0.169 | 0.118 |
| Ex. 8 | 466 | 842.65 |  | 0.154 | 0.104 |
| Ex. 9 | 127 | 868.19 | 2205 | 0.165 | 0.106 |
| Ex. 10 | 140 | 811.44 | 2374 | 0.122 | 0.118 |
| Ex. 11 | 202 | 713.95 |  | 0.155 | 0.111 |

As one can see form the table above, examples containing PTFE yarn (Examples 1-9) has slightly higher MVTR (~840-900 g/m$^2$/24 hrs) than the polyester examples (Examples 10-11) (~700-800 g/m$^2$/24 hrs). Comparing Examples 1, 5, and 7 (knitted with the flat back mesh construction as shown in FIG. 3) had much higher MVTR values in the military method, where there is airflow at the top of the jar compared to Examples 10 and 13 (without the PTFE yarns). This indicates the moisture vapor transmission is induced by the airflow.

In terms of cooling effect, the higher the Q-max, cooler the fabric feels to its touch. The Q-max measurement using Kawabata thermal tester (Thermo Labo) showed higher Q-max values on both sides of the fabric of Examples 1-9 compared to Examples 10-11.

| Sample ID | Intrinsic Thermal resistance ($R_{cf}$) ($\Delta°$ C.)(m$^2$)/W | Apparent intrinsic evaporative resistance ($R_{ef}$) ($\Delta$kPa)(m$^2$)/W | Total Thermal Resistance ($I_t$) Clo | Heat loss (Qt) W/m$^2$ | Thickness mm |
|---|---|---|---|---|---|
| Ex. 1 | 0.004 | 0.00206 | 0.492 | 869.36 | 0.42 |
| Ex. 2 | 0.006 | 0.00264 | 0.506 | 798.26 | 0.57 |
| Ex. 3 | 0.007 | 0.00247 | 0.509 | 812.34 | 0.5 |
| Ex. 4 | 0.007 | 0.00098 | 0.512 | 1008.92 | 0.35 |
| Ex. 5 | 0.004 | 0.00137 | 0.493 | 959.05 | 0.41 |
| Ex. 6 | 0.006 | 0.00228 | 0.502 | 837.11 | 0.57 |
| Ex. 7 | 0.006 | 0.0018 | 0.504 | 891.68 | 0.45 |
| Ex. 8 | 0.004 | 0.00107 | 0.491 | 1009.41 | 0.31 |
| Ex. 9 | 0.01 | 0.00181 | 0.532 | 871.17 | 0.62 |
| Ex. 10 | 0.009 | 0.00235 | 0.525 | 814.05 | 0.62 |

Total heat loss was measured using a large sweating guarded hot plate as per ASTM F1868 part C and data is summarized in the table above. This measurement confirmed that intrinsic thermal resistance of PTFE yarn based knits with flat back mesh construction fabric (Ex. 1-8) is lower compared to all polyester fabrics (Ex. 10). The evaporative resistance of PTFE containing knits (Ex. 1-8) are lower compared to the all polyester knit (Ex. 10). Lower thermal resistance along with lower evaporative together yielded fabrics with impressive up to 25% improvement in the total heat loss, comparing Ex. 1-8 with Ex. 10.

In conclusion, excellent Q-max, excellent thermal conductivity (lower resistance), lower evaporative resistance, higher heat loss for PTFE based flat back mesh knits (Examples 1-8). All these properties are important for active cooling application in textile.

Examples 11-13 compared to Example 1 explore peel strength adhesion between a knit fabric and pig skin. To test the examples, a 2"×4" sample of the knit fabric was placed on the dermis/hypodermis of pig skin with bovine serum and then 3 layers of gauze were placed on the knit layer. The samples were then dried for 16 hours at 37° C. Peel strength was then measured.

| Example | Commercial name | Description | Peak Load [lbf] | Adjusted Peak Load [lbf] | Peel Energy [in*lbf] |
|---|---|---|---|---|---|
| Ex. 11 | TRITEC ® silver dressing available from Milliken & Co | polyester/nylon bilayer knit | 0.334 | 0.331 | 0.322 |
| Ex. 12 | ASSIST ® silver dressing available from Milliken & Co | polyester/nylon bilayer fabric with non-stick backing | 0.236 | 0.232 | 0.283 |
| Ex. 13 | Fine mesh gauze (6 layers) | Rayon/polyester nonwoven | 0.591 | 0.544 | 1.16 |
| Ex. 1 | | 69%/31% PTFE/polyester | 0.043 | 0.005 | 0.02 |

As one can see from the chart above, the peak load, adjusted peak load, and the peel strength of the commercial examples 11-13 were significantly higher than the example 1 meaning that example 1 peeled off from the pig skin much easier than examples 11-13. Preferably, the peel test (according to this testing method), is less than about 0.1 in*lbf, more preferably less than 0.05 in*lbf.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the subject matter of this application (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the subject matter of the application and does not pose a limitation on the scope of the subject matter unless otherwise claimed. No language in the specification should be construed as indicating any non-claimed element as essential to the practice of the subject matter described herein.

Preferred embodiments of the subject matter of this application are described herein, including the best mode known to the inventors for carrying out the claimed subject matter. Variations of those preferred embodiments may become apparent to those of ordinary skill in the art upon reading the foregoing description. The inventors expect skilled artisans to employ such variations as appropriate, and the inventors intend for the subject matter described herein to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

What is claimed is:

1. A medical device comprising a device that covers at least a portion of a patient's skin, wherein the device has an inner surface and an outer surface, wherein the inner surface is designed to be in contact with the patient's skin, wherein the inner surface of the device comprises a multi-ply knit fabric having an upper and lower surface and a length and width, wherein the fabric comprises:
   a first knit ply comprising a plurality of first yarns, wherein the first knit ply forms the upper surface of the fabric;
   a second knit ply comprising a plurality of polytetrafluoroethylene (PTFE) yarns, wherein the PTFE yarns have a density of about 2 to 2.3 g/cm$^3$, a transmission in the IR region of 8-10 µm at least about 40%, and a thermal conductivity of at least about 0.2 W/(m·K), wherein the second knit ply forms the lower surface of the fabric;
   wherein the first ply and the second ply integrated through combined portions formed by at least one method selected from the group consisting of interlacing first yarns among the PTFE yarns of the second knit ply, interlacing PTFE yarns among the first yarns of the first knit ply, and interlacing a plurality of third yarns among the first yarns of the first knit ply and the PTFE yarns of the second knit ply; and,
   a composition comprising at least one silver ion-containing compound on at least the upper surface of the multi-ply knit fabric;
   wherein the multi-ply knit fabric is positioned such that the lower surface of the multi-layer knit fabric is adjacent the patient's skin.

2. The medical device of claim 1, wherein the PTFE yarns have a generally rectangular cross-sectional shape.

3. The medical device of claim 1, wherein the fabric comprises less than about 75% by weight PTFE yarns.

4. The medical device of claim 1, wherein the fabric comprises less than about 50% by weight PTFE yarns.

5. The medical device of claim 1, wherein the second knit ply comprises at least about 90% by weight PTFE yarns.

6. The medical device of claim 1, wherein the PTFE yarns comprise a density of about 2.15 to 2.25 g/cm$^3$.

7. The medical device of claim 1, wherein the PTFE yarns comprise a transmission in the IR region of 8-10 µm at least about 60%.

8. The medical device of claim 1, wherein the PTFE yarns comprise a thermal conductivity of at least about 0.23 W/(m·K).

9. The medical device of claim 1, wherein the rectangular cross-sectional shape of the PTFE yarns has a width to height ratio of between about 20:1 to 100:1.

10. The medical device of claim 1, wherein the lower surface of the fabric has a surface roughness of less than about 500 μm.

11. The medical device of claim 1, wherein the multi-ply knit fabric comprises a composition on at least the upper surface of the multi-ply knit fabric, wherein the composition comprises at least one silver ion-containing compound.

12. The medical device of claim 11, wherein the at least one silver ion-containing compound is selected from the group consisting of silver ion exchange materials, silver particles, silver salts, silver glass, and mixtures thereof.

13. The medical device of claim 12, wherein the silver ion exchange material is selected from the group consisting of silver zirconium phosphate, silver calcium phosphate, silver zeolite, and mixtures thereof.

14. The medical device of claim 12, wherein the silver ion exchange material is silver zirconium phosphate.

15. The medical device of claim 1, wherein the composition further comprises a binding agent selected from the group consisting of polyurethane binders, acrylic binders, and mixtures thereof.

16. The medical device of 15, wherein the binding agent is a polyurethane-based material.

17. The medical device of claim 1, wherein the medical device comprises a cast.

18. The medical device of claim 1, wherein the medical device comprises a compression device.

19. The medical device of claim 1, wherein the medical device comprises a decompression device.

* * * * *